United States Patent [19]

Greene et al.

[11] 4,143,230

[45] Mar. 6, 1979

[54] MANUFACTURE OF 2-(ALKYL, ALKENYL OR ALKYNYL) 3-CARBALKOXYALKYL KETONES FROM ALPHA, BETA-UNSATURATED KETONES

[75] Inventors: Andrew E. Greene, St. Martin d'Uriage; Pierre Crabbé, Meylan, both of France

[73] Assignee: CHON Corporation, Cambridge, Mass.

[21] Appl. No.: 736,469

[22] Filed: Oct. 28, 1976

[51] Int. Cl.$^2$ ............................................. C07C 51/34
[52] U.S. Cl. ............................... 562/504; 260/586 R; 260/586 C; 560/122
[58] Field of Search ................. 260/514 K, 468 K

[56] References Cited

U.S. PATENT DOCUMENTS 3,754,016  8/1973  Oberhansli .................... 260/468

*Primary Examiner*—Robert Gerstl
*Attorney, Agent, or Firm*—Ostrolenk, Faber, Gerb & Soffen

[57] ABSTRACT

The copper enolate of 3-allylcyclopentanone is alkylated with an alkyne so as to form the 2-alkynyl, 3-allyl-cyclopentanone which is then subjected to ozonolysis and oxidative cleavage to form 2-alkynylcyclopentan-3-one-1-yl alkylcarboxlic acid. The acid can be esterified to form a 2-alkynyl-3-carbalkoxyalkyl ketone which, in turn, can be hydrogenated to convert the alkynyl moiety to alkenyl or alkyl moieties. The procedure is particularly useful in the synthesis of methyl dl-jasmonate, dehydrojasminate and dihydrojasmonate.

11 Claims, No Drawings

MANUFACTURE OF 2-(ALKYL, ALKENYL OR ALKYNYL) 3-CARBALKOXYALKYL KETONES FROM ALPHA, BETA-UNSATURATED KETONES

Methyl jasmonate is found in *Jasminum grandiflorum L.* and is essential for the characteristic odor of jasmin. The corresponding acid is also known as a green plant growth inhibitor. Because of the importance of methyl jamonate, it has been the objective of several published chemical synthesis, all of which however, require at least seven steps and afford yields on the order of 30% or less. See, e.g., *Synthetic Comm.*, 4, 265 (1974), *J. Org. Chem.* 40, 2221 (1975) and German Pat. No. 2,508,295.

A synthesis has now been discovered which is shorter and which gives higher yields than those processes known heretofore. The new process involves a conjugate addition-alkylation of cyclopentenone followed by a selective ozonolysis and uses an allyl group as an acetic acid synthon for the conjugate addition-alkylation reaction. In addition, the process described below permits one to prepare a number of compounds structurally related to methyl jasmonate.

The new process involves the conjugate addition of an allyl copper reagent to cyclopentanone thereby forming the copper enolate of 3-allkylcyclopentanone which is alkylated with a suitable alkyne, e.g., an alkyne halide such as 1-iodo-2-pentyne. The conjugate addition of an organo copper reagent to a cyclic alpha, beta-unsaturated ketone so as to form the copper enolate and the subsequent alkylation of the enolate is well known. See, e.g., J. Amer. Chem. Soc., 97, 107 (1975), J. Org. Chem., 39, 275 (1974) and *Tetrahedron Letters*, 3345 (1973). The procedures of the prior art can be used in this invention provided, of course, that the organo copper reagent is an allyl copper reagent and the alkylating agent is an alkyne.

Cyclopentanone enolates have a well known tendency to undergo rapid proton transfer reactions leading to equilibration. It was therefore most surprising and unexpected to find that by using the allyl copper reagent and the alkyne, the resulting trans 2-alkynyl, 3-allylcyclopentanone was selectively produced with only relatively small amounts of dialkylated material and no appreciable amount of any position isomer or of the cis isomer. As a result, there is no necessity to effect a tedious separation of isomers, a problem inherent in many of the prior art synthesis.

The trans 2-alkynyl, 3-allylcyclopentanone is then subjected to ozonolysis following conventional procedures (see e.g., *Tetrahedron Letters*, 1387 (1974); Chem. Rev., 58,925 (1958)), and the ozonolysis product oxidatively cleaved by contact with, e.g., Jones reagent or silver oxide to produce the 2-alkynylcyclopentan-3-one-1-yl alkylcarboxylic acid. In order to maximize the yield of the product, it is preferred to react the ozonolysis product with dimethyl sulfide before treatment with Jones reagent. When the alkyne is pentyne, the acid produced is dehydrojasmonic acid.

In order to convert the acid into the 2-alkynyl, 3-carbalkoxyalkyl ketone, the acid is esterified with an appropriate esterifying agent such as diazomethane or an alcohol such as methanol in the presence of a strong acid such as a mineral acid (hydrochloric or sulfuric acid) or organic acid (p-toluene sulfonic acid).

It will be noted that the acetylenic bond is completely stable under the procedure described above. The triple bond can be converted by hydrogenation into a double bond or can be completely saturated by selection of an appropriate hydrogenation catalyst. Thus, when it is desired to obtain the 2-alkenyl ketone, use of the Lindlar catalyst is appropriate and when it is desired to saturate the acetylenic bond, use of paladium as the hydrogenation catalyst is appropriate.

The reactions involved in this process are essentially stoichiometric so that the amounts of reagents can be varied over a large range, the reagent present in stoichiometric deficiency determining the amount of product produced.

The following is an example of how the present process can be used to produce dehydrojasmonic acid, methyl dehydrojasmonate, methyl dl-jasmonate, and methyl dl-dihydrojasmonate.

n-Butyllithium in hexane (150 ml, ca. 1.8 M, ca. 270 mmol) was slowly added to a stirred solution of 30 g of 1-butyne in 250 ml of tetrahydrofuran at $-78°$ under nitrogen. After 2 additional hours at $-78°$, the solution was allowed to warm to 0° and was treated with 15 g of paraformaldehyde in one portion. The resulting mixture was stirred for 2.5 hours at room temperature. The mixture was then diluted with ether, washed successively with water and aqueous sodium chloride solution, dried over potassium carbonate, filtered, and concentrated carefully under reduced pressure. Distillation of the resulting material (75° at 28 mm) gave 22.5 g of 2-pentyn-1-ol as a clear oil (99%).

Phosphorus tribromide (10.7 ml, 30.8 g, 114 mmol) was added over 5 minutes to a stirred solution of 22.4 g (267 mmol) of the above alcohol in 49 ml of diethyl ether and 4.9 ml of pyridine at 0°. Following the addition, the reaction mixture was refluxed for 2.5 hours, left at room temperature overnight and then poured into dilute sodium bicarbonate solution. Extraction with ether and washing the organic phase successively with dilute hydrochloric acid, dilute sodium bicarbonate and water, followed by drying over sodium sulfate, filtration and careful removal of solvent under reduced pressure afforded the crude product. Distillation (61°-65° at 30 mm) gave 29.5 g of 1-bromo-2-pentyne as a clear oil (75%).

A mixture of 3.0 g (2.04 mmol) of the above bromide, 6 g (4.0 mmol) of sodium iodide, and 60 ml of acetone was stirred under argon, protected from light, for 8 hours. An ether-hexane solution was then added, the resulting precipitation was filtered, and the filtrate was freed from solvent under reduced pressure. The crude product was then filtered through 30 g of silica gel using 1% ether-hexane to afford 3.0 g of the light-sensitive 1-iodo-2-pentyne as a pale yellow oil (76%).

Lithium wire (2.1 g, 303 mmol) in small pieces in 26 ml of dry tetrahydrofuran containing a trace of naphthalene under argon was cooled to $-15°$ and was treated with 3.32 g (24.8 mmol) of allyl phenyl ether in 14 ml of tetrahydrofuran containing a trace of naphthalene, with rapid stirring for 45 minutes. After an additional 1.25 hours at room temperature, 14.7 ml (ca. 6.6 mmol) of the allyllithium solution was added at $-15°$ over 2 minutes to 635 mg (3.3 mmol) of copper iodide in 10 ml of tetrahydrofuran under argon with rapid stirring. After 5 minutes, the dark solution was of lithium diallylcuprate cooled to $-78°$ and 245 mg (3.0 mmol) of cyclopentenone in 2 ml of tetrahydrofuran was added over 2 minutes. After 40 minutes at $-78°$, 1 ml of tetramethylethylenediamine was added followed 5 minutes later by 3.0 g (15.5 mmol) of 1-iodo-2-pentyne in 10 ml of hexamethylphosphoramide. After 2 additional hours at $-78°$, 1 ml of methanol was added and the mixture was poured into aqueous ammonium chloride-ammonium hydroxide-ether. After rapidly stirring for 15 minutes, the organic phase was separated and washed successively with aqueous sodium hydroxide, aqueous hydrochloric acid, aqueous sodium thiosulfate, and aqueous sodium chloride. After drying over potassium carbonate, the solvent was removed under reduced pressure and the resulting oil was chromatographed on silica gel using chloroform-hexane to afford 325 mg of 2-pentynyl, 3-allylcyclopentanone (57%).

A stirred solution of 216 mg (1.13 mmol) of the 2-pentynyl, 3-allylcyclopentanone in 2.3 ml of methanol and 1.15 ml of methylene chloride was cooled to −78° and treated with a stream of ozonized oxygen. After the disappearance of the starting material, 1.15 ml of dimethyl sulfide was added and the solution was then stirred at room temperature for 1 hour, after which time the solvent was evaporated under reduced pressure. The resulting oil was dissolved in 6 ml of acetone and at 0° treated with 1.5 ml of Jones reagent over 45 minutes. Isopropyl alcohol was then added to destroy the excess reagent and the product was isolated with ethyl acetate, affording 224 mg of crude dehydrojasmonic acid.

The above acid at room temperature was esterified using excess ethereal diazomethane and the resulting ester was then evaporatively distilled (75° at 0.2 mm) to give 207 mg of methyl dehydrojasmonate (82%).

A mixture of 97 mg (0.44 mmol) of the above acetylenic ester and 25 mg of 5% palladium on carbon in 10 ml of ethyl acetate was stirred rapidly under a hydrogen atmosphere for 4.5 hours. The hydrogen was then removed, the mixture was filtered and the resulting solution was concentrated under reduced pressure. Evaporative distillation (60° at 0.1 mm) then afforded 97 mg of methyl dl-dihydrojasmonate (98%).

A mixture of 68 mg (0.31 mmol) of the acetylenic ester and 35 mg of Lindlar catalyst in 5 ml of acetone was stirred rapidly under a hydrogen atmosphere for 1 hour. The hydrogen was then removed, the mixture was filtered and the resulting solution was concentrated under reduced pressure. Evaporative distillation (60° at 0.1 mm) then afforded 69 mg of methyl dl-jasmonate (100%).

The methyl dl-jasmonate and methyl dl-dihydrojasmonate were obtained in nearly quantitative yields from methyl dehydrojasmonate and displayed spectral and chromatographic properties in complete agreement (except for rotation) with those of authentic samples.

Various changes and modifications can be made in the process of the present invention without departing from the spirit and scope thereof. The various embodiments set forth herein were for the purpose of illustrating the invention but were not intended to limit it.

We claim:

1. A simple, high yield process which comprises effecting the conjugate addition of an allyl copper reagent to cyclopentenone so as to form the copper enolate of 3-allylcyclopentanone; alkylating the enolate with a pentyne so as to form the trans 2-pentyne, 3-allylcylopentanone; subjecting the trans 2-pentyne, 3-allylcyclopentanone to ozonolysis and oxidatively cleaving the ozonolysis product so as to form dehydrajasmonic acid.

2. The process of claim 1 wherein the carboxylic acid is esterified so as to form the corresponding 2-pentyne, 3-carbalkoxyalkyl ketone.

3. The process of claim 2 wherein the 2-pentyne, 3-carbalkoxyalkyl ketone is hydrogenated.

4. The process of claim 3, wherein the ozonolysis product is mixed with dimethyl sulfide and then oxidatively cleaved with Jones reagent.

5. The process of claim 2 wherein said acid is esterified with a methyl group whereby methyl dehydrojasmonate is obtained.

6. The process of claim 5 wherein the ozonolysis product is mixed with dimethyl sulfide and then oxidatively cleaved with Jones reagent, and wherein the acid is esterified using diazomethane as the esterifying agent.

7. The process of claim 6 wherein said methyl dehydrojasmonate is hydrogenated in the presence of the Lindlar catalyst whereby methyl dl-jasmonate is obtained.

8. The process of claim 6 wherein said methyl dehydrojasmonate is hydrogenated in the presence of palladium whereby methyl dl-dihydrojasmonate is obtained.

9. The process of claim 3 wherein the 2-pentyne, 3-carbalkoxyalkyl ketone is hydrogenated in the presence of the Lindlar catalyst to produce the corresponding 2-pentene 3-carbalkoxyalkyl ketone.

10. The process of claim 3, wherein the 2-pentyne 3-carbalkoxyalkyl ketone is hydrogenated in the presence of palladium to produce the corresponding 2-pentyl, 3-carbalkoxyalkyl ketone.

11. The process of claim 1 wherein said reagent is lithium diallylcuprate and said conjugate addition is effected at −78° in tetrahydrofuran, wherein said pentyne is 1-iodo-2-pentyne and said alkylation is effected in hexamethylphosphoramide whereby trans 2-pentynyl, 3-allylcyclopentanone is formed, wherein said ozonolysis is effected in methanol-methylene chloride by contact with a stream of ozonized oxygen at −78° and said oxidative cleavage is effected by contacting the ozonolysis product with Jones reagent at 0° C so as to form said dehydrojasmonic acid.

* * * * *